US010183868B2

(12) United States Patent
McCormick et al.

(10) Patent No.: US 10,183,868 B2
(45) Date of Patent: Jan. 22, 2019

(54) MESOPOROUS ZINC OXIDE POWDER AND METHOD FOR PRODUCTION THEREOF

(71) Applicant: Antaria Limited, Bentley, Western Australia (AU)

(72) Inventors: Paul McCormick, Perth (AU); Geoffrey Trotter, Yokine (AU)

(73) Assignee: ANTARIA LIMITED, Bentley, Western Australia ( * ) Notice: Subject to any disclaimer, the term of this patent is extended or adjusted under 35 U.S.C. 154(b) by 636 days.

(21) Appl. No.: 14/850,281

(22) Filed: Sep. 10, 2015

(65) Prior Publication Data

US 2015/0376025 A1    Dec. 31, 2015

Related U.S. Application Data

(60) Division of application No. 12/833,168, filed on Jul. 9, 2010, which is a continuation of application No. PCT/US2009/030732, filed on Jan. 12, 2009.

(60) Provisional application No. 61/006,398, filed on Jan. 11, 2008.

(30) Foreign Application Priority Data

Jul. 2, 2008 (AU) .................................. 2008903390

(51) Int. Cl.
| | |
|---|---|
| *C01G 9/00* | (2006.01) |
| *C01G 9/02* | (2006.01) |
| *A61K 8/27* | (2006.01) |
| *A61Q 17/04* | (2006.01) |

(52) U.S. Cl.
CPC .................. *C01G 9/02* (2013.01); *A61K 8/27* (2013.01); *A61Q 17/04* (2013.01); *A61K 2800/262* (2013.01); *C01P 2004/03* (2013.01); *C01P 2004/45* (2013.01); *C01P 2004/51* (2013.01); *C01P 2006/12* (2013.01); *C01P 2006/14* (2013.01); *C01P 2006/17* (2013.01); *C01P 2006/60* (2013.01); *Y10T 428/2982* (2015.01)

(58) Field of Classification Search
CPC ....................................................... C01G 9/02
USPC ........ 423/622, 105; 424/401, 641–643, 614; 516/88
See application file for complete search history.

(56) References Cited

U.S. PATENT DOCUMENTS

| | | | |
|---|---|---|---|
| 2,144,299 A * | 1/1939 | Sessions .................. | C01G 9/00 423/206.2 |
| 5,032,390 A | 7/1991 | Iwaya et al. | |
| 5,441,726 A | 8/1995 | Mitchnick et al. | |
| 5,527,519 A * | 6/1996 | Miksits .................... | A61K 8/27 423/622 |
| 5,576,354 A | 11/1996 | Deflandre et al. | |
| 5,587,148 A | 12/1996 | Mitchell et al. | |
| 5,587,150 A | 12/1996 | Deflandre et al. | |
| 5,827,508 A | 10/1998 | Tanner et al. | |
| 5,849,273 A | 12/1998 | Bonda et al. | |
| 5,863,514 A | 1/1999 | Sasaki et al. | |
| 5,985,251 A | 11/1999 | Gonzenbach et al. | |
| 6,033,649 A | 3/2000 | Gonzenbach et al. | |
| 6,071,501 A | 6/2000 | Robinson | |
| 6,171,580 B1 * | 1/2001 | Katsuyama ............. | A61K 8/27 423/622 |
| 6,203,768 B1 | 3/2001 | McCormick | |
| 6,277,892 B1 | 8/2001 | Deckner et al. | |
| 6,444,195 B1 | 9/2002 | Cole | |
| 6,492,326 B1 | 12/2002 | Robinson et al. | |
| 6,503,475 B1 | 1/2003 | McCormick et al. | |
| 7,075,229 B2 | 7/2006 | Lambertini et al. | |
| 7,235,587 B2 | 6/2007 | Bonda et al. | |
| 7,244,416 B2 | 7/2007 | Meyer et al. | |
| 7,718,261 B2 | 5/2010 | Katusic et al. | |
| 2004/0180020 A1 | 9/2004 | Manelski et al. | |
| 2005/0142095 A1 | 6/2005 | Scancarella et al. | |
| 2006/0188432 A1 | 8/2006 | Shio | |
| 2008/0220026 A1 | 9/2008 | Maitra et al. | |
| 2009/0010971 A1 | 1/2009 | Shio et al. | |

(Continued)

FOREIGN PATENT DOCUMENTS

| | | | |
|---|---|---|---|
| DE | 2404049 | * | 8/1975 |
| EP | 0992455 | A | 4/2000 |
| EP | 1892218 | A | 2/2008 |

(Continued)

OTHER PUBLICATIONS

Advanced Nanotechnology Ship First Commercial Sales of ZinClear, 2007, pp. 1-3.

(Continued)

Primary Examiner — Steven J Bos
(74) Attorney, Agent, or Firm — Edell, Shapiro & Finnan, LLC

(57) ABSTRACT

A method of manufacturing a zinc oxide powder including synthesizing a mesoporous zinc oxide precursor powder by adding an aqueous solution of zinc chloride to an aqueous solution of sodium carbonate while agitating to cause precipitation of a mesoporous zinc carbonate powder wherein the molar ratio of zinc chloride to sodium carbonate present when the aqueous solution of zinc chloride and the aqueous solution of sodium carbonate are reacted is at least 1:2, heat treating a mesoporous zinc precursor material to form the mesoporous zinc oxide powder at a heat treatment temperature in the range of 250-575° C. The zinc oxide powder includes mesoporous zinc oxide aggregates with a plurality of primary zinc oxide crystallites bonded together at shared interfaces.

15 Claims, 5 Drawing Sheets

(56) References Cited

U.S. PATENT DOCUMENTS

2009/0155194 A1    6/2009  Meyer et al.
2010/0074837 A1*   3/2010  Shio .................... A61K 8/27
                                                    423/622

FOREIGN PATENT DOCUMENTS

| WO | 9524359    A  | 9/1995  |
|----|---------------|---------|
| WO | 03080515   A1 | 2/2003  |
| WO | 2006010214 A1 | 2/2006  |
| WO | 2006129793 A1 | 12/2006 |
| WO | 2007123309 A1 | 11/2007 |

OTHER PUBLICATIONS

International Search Report in PCT/US2009/30732, dated Apr. 23, 2009, 4 pages.

Hiller et al., "Reversibly Erasable Nanoporous Anti-Reflection Coatings from Polyelectrolyte Multilayers", 2002, vol. 1, Nature Publishing Group, pp. 59-63.

L. Jing et al., "The Surface Properties and Photocatalytic Activities of ZnO Ultrafine Particles", Applied Surface Science, vol. 180, pp. 308-314, Jul. 2001.

Colipa, "Method for the in Vitro Determination of UVA Protection Provided by Sunscreen Products", 2007, pp. 1-20.

* cited by examiner

MESOPOROUS ZINC OXIDE POWDER AND METHOD FOR PRODUCTION THEREOF

CROSS REFERENCE TO RELATED APPLICATIONS

This application is a divisional of U.S. patent application Ser. No. 12/833,168, filed Jul. 9, 2010, entitled "Mesoporous Zinc Oxide Powder and Method for Production Thereof", which is a continuation of PCT/US2009/30732, filed Jan. 12, 2009, entitled "Mesoporous Zinc Oxide Powder and Method for Production Thereof", which claims priority from U.S. Provisional Patent Application Ser. No. 61/006,398, filed Jan. 11, 2008, entitled "Mesoporous Zinc Oxide Powder and Method for Production Thereof", and which also claims priority from Australian Provisional Patent Application No. 2008903390, filed Jul. 2, 2008, and titled "Mesoporous Zinc Oxide Powder and Method for Production Thereof". The entire contents of these applications are hereby incorporated by reference in their entireties.

FIELD OF THE INVENTION

The present invention is directed to a powder consisting of mesoporous zinc oxide aggregates and a method of manufacturing the same, for use in visibly-transparent compositions that provide broad-spectrum photoprotection when applied to a substrate.

BACKGROUND OF THE INVENTION

It is well-known in the art that zinc oxide (ZnO) blocks ultraviolet (UV) radiation at wavelengths from 290 nm up to about 375 nm. In addition, zinc oxide has long been utilized for its antimicrobial and other properties. Despite these beneficial properties, use of zinc oxide has been limited primarily due to an undesirable whitening effect on the substrate to which a zinc oxide-containing product was applied. To the extent that zinc oxide was incorporated into dispersions for cosmetic and sunscreen formulations and products, formulators minimized ZnO levels and/or users applied the product sparingly or at levels lower than indicated to reduce or minimize whitening. In so doing, however, the photoprotective efficacy of the product was lessened. Similarly, such whitening was and is undesirable in photoprotective transparent coatings and transparent plastic films.

Whitening on a substrate (e.g., skin) after application of a photoprotective product containing dispersed ZnO powder is attributable to scattering of light from the particles in the backward direction (i.e., away from the substrate and toward the viewer). In contrast, light scattered in the forward direction (through the substrate) contributes to the transmittance of light. This is known in the art as "diffuse" transmittance. Total transmittance of incident light through a ZnO-containing photoprotective product is thus comprised of light that is diffusely transmitted as well as light that is transmitted without scattering, known in the art as "specular" transmittance.

The main factors that affect the scattering of light from particles and hence whitening include the particle size and the refractive index of the particles relative to the media in which the particles are dispersed. In general, decreasing the size of the particles or the relative refractive index of the particles causes a decrease in scattering and whiteness of the product.

Prior art approaches to the problem of surface whitening caused by ZnO-containing photoprotective products have concentrated largely on reducing the average size of the zinc oxide particles in the product to below at least 0.2 micrometers. This particle size reduction decreases the scattering of light from the particle surfaces which increases transparency and reduces whiteness. For example, U.S. Pat. No. 5,587,148 teaches a substantially visibly transparent topical sunblock formulation comprising a dispersion of micronized particles of zinc oxide having an average particle diameter of less than about 0.2 micrometers. U.S. Pat. No. 5,032,390 teaches sunblock compositions comprising from 1% to 25% by weight of particulate zinc oxide having an average particle size of from 0.07 microns to 0.3 microns. The disclosed compositions are further taught to include from 1% to 25% of particulate titanium dioxide having an average particle size of from 0.03 microns to 0.07 microns.

Reduction of ZnO particle size to nanoscale (e.g., particularly less than about 0.1 microns) is not, however, without consequences. Nanosize ZnO particles have been associated with a high level of photocatalytic activity associated with the formation of free radicals and, resulting in degradation of polymeric ingredients typically contained in cosmetics, plastics, and paints. Moreover, in photoprotective personal care products, high photocatalytic activity can produce free radicals which have been reported to cause deleterious health effects.

The greater available surface area of nano-sized particles may increase the amount of flocculation and, in turn, agglomeration. Photoprotective products containing nano-sized particles therefore may be unstable and, in the case of emulsions, phase separation. This instability can lead to higher scattering of light and increased whiteness than would otherwise be expected based on particle size alone, as well as a reduced level of photoprotection.

Recently, concerns have been raised regarding potential negative health consequences of transdermal penetration of nano size inorganic particles and systemic absorption of organic sunscreen filters and their breakdown products. Irrespective of whether or the extent to which these concerns are substantiated, there has been and remains an as yet unmet need for topical photoprotective compositions that minimize or, preferably, do not contain organic sunscreen filters and/or nano-sized physical sunscreen blocking agents. There remains a need for zinc oxide powders, that are of a sufficiently large size to not raise concerns about product safety or stability, that when dispersed in a transparent matrix provide substantial visible transparency combined with minimal or no whitening.

Alternative to reducing particle size, the intensity of light scattered at particle interfaces can be decreased by reducing the difference in the refractive index across the interface. For example, nanoporous films and coatings are known to exhibit improved transparency and reduced reflection associated with the reduction in the relative refractive index associated with the film structure. For example, Hiller et al (Nature Materials, 2002, 1, 59-63) describe nanoporous polymer films with increased light transmission and reduced reflection. U.S. Pat. No. 7,075,229 teaches a light-emitting device incorporating a transparent nanoporous alumina film. US Patent Publication Application No. 2006/0188432 teaches a method of producing porous titanium oxide powder with improved transparency.

There has been and there remains a need for transparency to be achieved using a dispersion of zinc oxide powders that are not predominately comprised of nano-sized particles. This need is met by embodiments of the present invention.

SUMMARY OF THE INVENTION

According to one aspect of the present invention there is provided a zinc oxide powder which, when used in a dispersion at a concentration of at least 50 wt % of zinc oxide, produces a transparent composition having a total visible transmittance through a path length of 20 microns at 550 nm of at least one of; at least 70%, at least 75%, at least 80% or at least 85%, the powder having a number average zinc oxide aggregate size of at least 0.8 microns or at least 1 micron.

According to a second aspect of the present invention there is provided a zinc oxide powder which, when used in a dispersion at a concentration of at least 40 wt % of zinc oxide, produces a transparent composition having a total visible transmittance through a path length of 20 microns at 550 nm of at least one of; at least 70%, at least 75%, at least 80% or at least 85%, the powder having a number average zinc oxide aggregate size of at least 0.8 microns or at least 1 micron.

According to a third aspect of the present invention there is provided a zinc oxide powder which, when used in a dispersion at a concentration of at least 30 wt % of zinc oxide, produces a transparent composition having a total visible transmittance through a path length of 20 microns at 550 nm of at least one of; at least 70%, at least 75%, at least 80% or at least 85%, the powder having a number average zinc oxide aggregate size of at least 0.8 microns or at least 1 micron.

According to a fourth aspect of the present invention there is provided a zinc oxide powder which, when used in a dispersion at a concentration of at least 20 wt % of zinc oxide, produces a transparent composition having a total visible transmittance through a path length of 20 microns at 550 nm of at least one of; at least 70%, at least 75%, at least 80% or at least 88%, the powder having a number average zinc oxide aggregate size of at least 0.8 microns or at least 1 micron. According to a fifth aspect of the present invention there is provided a zinc oxide powder which, when used in a dispersion at a concentration of at least 10 wt % of zinc oxide produces a transparent composition having a total visible transmittance through a path length of 20 microns at 550 nm of at least one of; at least 75%, at least 80%, at least 85% or at least 93%, the powder having a number average zinc oxide aggregate size of at least 0.8 microns or at least 1 micron.

According to a sixth aspect of the present invention there is provided a zinc oxide powder which, when used in a dispersion at a concentration of at least 50 wt % zinc oxide produces a CIE whiteness index less than 30, or less than 40, or less than 50, the powder having a number average zinc oxide aggregate size of at least 0.8 microns or at least 1 micron.

According to a seventh aspect of the present invention there is provided a zinc oxide powder which, when used in a dispersion at a concentration of at least 30 wt % produces a CIE whiteness index less than 25, or less than 35, or less than 45, the powder having a number average zinc oxide aggregate size of at least 0.8 microns or at least 1 micron.

According to an eighth aspect of the present invention there is provided a zinc oxide powder which, when used in a dispersion at a concentration of at least 20 wt % produces a CIE whiteness index less than 25, or less than 35, or less than 45, the powder having a number average zinc oxide aggregate size of at least 0.8 microns or at least 1 micron.

According to a ninth aspect of the present invention there is provided a zinc oxide powder which, when used in a dispersion at a concentration of at least 10 wt % produces a CIE whiteness index less than 10, or less than 20, or less than 30, the aggregates having a number average aggregate size of at least 0.8 microns or at least 1 micron.

The zinc oxide powder of any one of first to ninth aspects of the present invention may be characterized in that the aggregates are mesoporous and have a total mesopore volume of at least 0.25 cm$^3$/g or at least 0.35 cm$^3$/g or at least 0.5 cm$^3$/g.

The aggregates may have sizes in the range of 0.1 to 100 microns. In one form, the number average zinc oxide aggregate size may be compared with a target aggregate size and reduced using milling if the number average zinc oxide aggregate size is larger than the target aggregate size.

In one form, the mesoporous zinc oxide powder, when used in a dispersion to provide a transparent composition, for a given weight percentage of zinc oxide added to the composition, the SPF of the composition may be greater than the SPF achieved for an equivalent composition comprising non-porous zinc oxide particles having a particle size equivalent to the number average zinc oxide aggregate size.

In one form, the refractive index of the powder is adjustable by filling the open mesopores of the aggregates with a substance other than air.

According to a tenth aspect of the present invention, there is provided a method of manufacturing the zinc oxide powder of any one of first to ninth aspects of the present invention, the method characterized in that a mesoporous zinc precursor material is heat treated to form the mesoporous zinc oxide powder at a temperature sufficiently low temperature to retain and increase the mesoporosity of the precursor material.

The mesoporous zinc precursor material may be heat treated to form the mesoporous zinc oxide powder at a heat treatment temperature in at least one of: the range of 250-575° C.; the range of 300-525° C.; the range of 350-475° C.; or the range of 400-450° C.

In one form, the method further comprises the step of synthesizing the mesoporous zinc oxide precursor powder by reacting an aqueous solution of zinc chloride with an aqueous solution of sodium carbonate whilst agitating to cause precipitation of a mesoporous zinc carbonate powder. In one form, the molar ratio of zinc chloride to sodium carbonate present when the aqueous solution of zinc chloride and the aqueous solution of sodium carbonate are reacted may be one of: at least 1:2 or at least 1:3.

According to an eleventh aspect of the present invention there is provided a zinc oxide powder in the form of aggregates substantially as herein described with reference to the examples and accompanying drawings. In one form, the zinc oxide powder is mesoporous.

According to a twelfth aspect of the present invention there is provided a zinc oxide powder in the form of aggregates when used in a dispersion to provide a transparent composition substantially as herein described with reference to the examples and accompanying drawings. In one form, the zinc oxide powder is mesoporous.

According to a thirteenth aspect of the present invention there is provided a method of manufacturing a zinc oxide powder substantially as herein described with reference to the examples and accompanying drawings. In one form, the zinc oxide powder is mesoporous.

BRIEF DESCRIPTION OF THE DRAWINGS

In order to facilitate a more detailed understanding of the nature of the invention, embodiments will now be described in detail, by way of example only, with reference to the accompanying drawings, in which.

DETAILED DESCRIPTION OF EMBODIMENTS OF THE INVENTION

Figure 1:
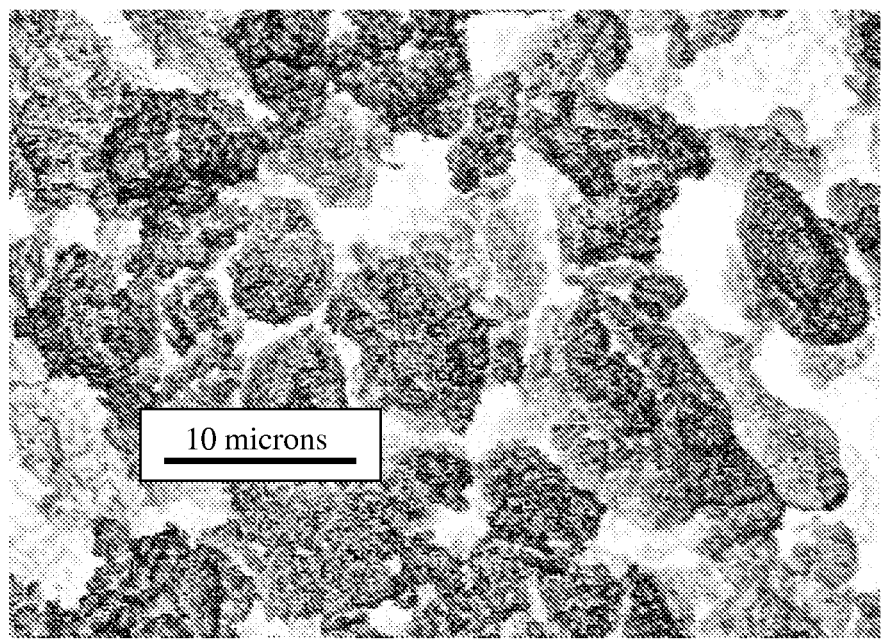
FIG. 1 is a high resolution scanning electron micrograph of the mesoporous zinc oxide powder from Example 1 at a low magnification showing the size of the aggregates.

Particular embodiments of the present invention are now described. The terminology used herein is for the purpose of describing particular embodiments only, and is not intended to limit the scope of the present invention. Unless defined otherwise, all technical and scientific terms used herein have the same meanings as commonly understood by one of ordinary skill in the art to which this invention belongs. Unless otherwise indicated, as used in the present application, numerical percentages refer to the percentage by weight of a specified ingredient relative to the total weight of the composition.

The term "aggregates" refer to a plurality of primary zinc oxide crystallites bonded together at shared interfaces. Because of the strong interfacial bonding between the primary crystallites, it is necessary to use mechanical comminution processes such as high energy bead milling to reduce the aggregate size. In this regard, an "agglomerate" differs from an "aggregate" in that the weaker bond between agglomerated crystallites allows agglomerates to be separated and dispersed using high shear mixing or similar lower energy mixing and dispersion processes.

The term "aggregate size" as used in this specification refers to the overall size of discrete unattached aggregates that are individually dispersed in a liquid, semi-solid or solid media. The "average aggregate size" is defined mathematically according to the following equation:

$$<d> = \Sigma f_i \cdot d_i$$

wherein
<d> is the average aggregate size;
$d_i$ is the aggregate diameter; and,
$f_i$ is the fraction of aggregates with a diameter value of $d_i$ The average aggregate size can be reported on an aggregate number weighted basis or a volume basis. Those skilled in the art will appreciate that for a given powder with a given distribution of particle sizes, the volume weighted average will always be greater than the number weighted average. The aggregate size can be expressed in terms of a distribution of aggregates as measured using microscopy, light scattering, acoustic scattering, sedimentation or other sizing techniques known to those of skill in the art In the description to follow, the size distribution of aggregates was measured using both static laser light-scattering and acoustic attenuation.

As used in this specification, the term "mesoporous" refers to pores ranging in size from about 2 nm to about 100 nm. The pores are categorized as "open pores" that connect through and open onto a surface of the aggregate or as "closed pores" that are sealed from fluid ingress from the surface of the aggregate. The distribution of pore sizes and total pore volume of the aggregates may be measured using gas adsorption and pycnometry or other techniques which are known to those of skill in the art.

The term "total envelope volume" is defined as the absolute volume of the aggregate based on its size. The total envelope volume is equal to the volume of zinc oxide actually present in the aggregate plus the total pore volume (which in turn is the sum of the volume of the closed pores and the volume of open pores).

The term "dispersed" refers to aggregates or powders that are suspended in and surrounded by a continuous phase. The term "dispersion" refers to a plurality of aggregates that are suspended within another substance, "the carrier". The aggregates will be substantially evenly distributed when dispersed within the carrier.

The term "a transparent composition" includes compositions having application as a cosmetic preparation, as a sunscreen, as a coating, in a plastic, as a cosmaceutical preparation, or as a pharmaceutical preparation. Advantageously the compositions are able to provide broad spectrum UV protection.

The mesoporous zinc oxide powder of the present invention is in the form of aggregates having sizes in the range of 0.1 to 100 microns, with 0.2 to 10 microns being preferable. Significantly, the aggregates of the present invention may be of sufficiently large size that potential safety issues do not arise. The number weighted average size of the aggregates in the present invention is greater than 0.8 microns although high transparency has been achieved using dispersions of the mesoporous zinc oxide powder with the average aggregate size being greater than 1 micron, or 1.5 micron and for volume weighted average size in the range of 3 microns to 10 microns.

The average aggregate size may be compared with a target aggregate size and adjusted if required. The average aggregate size can be adjusted to meet a target aggregate size using any number of suitable methods, for example the use of one or more sieves, grids, meshes, or screens which allow aggregate greater than a given size to be retained whilst aggregates smaller than a given size pass through a plurality of suitably sized apertures. The average aggregate size may equally be adjusted using other separation methods such as centrifugation classifiers, filtration, or cyclone separation. As well, the average aggregate size may be reduced to a given value by attrition bead milling in a fluid carrier.

The mesoporous zinc oxide powder of the present invention is characterized in that the aggregates have a total mesopore volume of at least 0.25 cm$^3$/g. Each aggregate comprises a plurality of zinc oxide crystallites having an average crystallite size in the range of 5 nm to about 50 nm and a high level of internal porosity, described in greater detail below.

The pore size of the aggregates is in the range of 2 nm to 100 nm, preferably in the range of 20 to 70 nm. The pores include both open pores that connect through the aggregate allowing fluid ingress from the surface of the aggregates and closed pores that are sealed against fluid ingress from the surface of the aggregates. The size distribution of open mesopores and the total volume of mesopores are measured using gas adsorption techniques known to those of skill in the art. By way of example, the mean open pore size of the aggregates is approximately 30 nm for a total volume of open pores greater than 0.35 $cm^3/g$. In one form of the present invention, the aggregates have a unimodal pore size distribution with the average pore size equal to 35 nm. The specific surface area measured by gas desorption is in the range 20-70 $m^2/g$.

In one form, the closed pores represent from 2% to about 15% of the total envelope volume of the aggregate as measured using helium gas pycnometry.

Best results in terms of high transparency are achieved when the mesoporous zinc oxide powder is dispersed in a carrier when the total pore volume is at least 50% of the total envelope volume of the aggregates. As a consequence of the presence of such a high total pore volume, the mesoporous zinc oxide powder has a tap density of less than 0.7 $g/cm^3$ as measured using standard techniques known to those skilled in the art. The envelope density of the aggregates is adjustable. When dispersed, the open mesopores of the aggregates can become filled with the carrier which may be a gas or a liquid, whilst the closed mesopores are filled with a gaseous phase, such as $CO_2$ or air. Filling of the open pores with a liquid phase of lower density than zinc oxide during dispersion provides higher stability against gravity induced settling during and following dispersion.

Without wishing to be bound by theory, it is understood that, due to the meso scale of the aggregate pore structure (<100 nm) and the size of the mesopores, the refractive index of the aggregates is equal to the volume weighted average of the refractive index of the air filled closed pores, the liquid filled open pores and the zinc oxide crystallites when the mesoporous zinc oxide powder is dispersed in a liquid carrier. Thus, as the volume of open mesopores increases the difference in refractive index of the aggregates relative to the carrier phase of the dispersion is reduced. The reduction in the relative refractive index of the aggregates decreases scattering, resulting in a decrease in the whiteness and an increase in transparency of dispersions containing the aggregates. Thus the mesoporous zinc oxide powder can be used in a dispersion to provide a transparent photoprotective composition having application in cosmetic preparations, as a sunscreen, as a coating, in a plastic, in pharmaceutical preparations, in cosmetic preparations, or as a ceramic raw material. The mesoporous zinc oxide powder of the present invention, when dispersed in a suitable carrier, enables the compositions to be highly transparent to visible radiation, while at the same time providing broad spectrum shielding from UV radiation.

For a given weight percentage of zinc oxide added to a composition, higher SPF values are achieved using the mesoporous zinc oxide powders of the present invention compared with the SPF values achieved for a composition comprising non porous zinc oxide particles of the equivalent size. Without wishing to be bound by theory, the mesoporous structure of the aggregates is understood to cause the UV absorption of the aggregates to be greater that the UV absorption non-porous zinc oxide powder of the same size. Thus the mesoporous zinc oxide powders can be used in a dispersion to provide photoprotective compositions that provide a desired SPF and broad spectrum protection while minimizing or, preferably, eliminating the need to add organic UV filters consisting of nano molecular lengths or the need to add nano-sized physical UV blocking agents.

The following examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

Example 1: Preparation of Mesoporous Zinc Carbonate Precursor

Zinc carbonate precursor powder was synthesized by reacting aqueous solutions of zinc chloride and sodium carbonate in the molar ratio of $1ZnCl_2:3Na_2CO_3$ at room temperature. The individual solutions consisted of 1230 g of zinc chloride dissolved in 4 L of deionized water and 960 g of sodium carbonate dissolved in 10 L of DI water. The zinc chloride solution was added under vigorous stifling to the carbonate solution resulting in a white precipitate. The precipitate was washed using deionized water to less than 100 ppm and dried at 120 degrees Celcius.

The crystal structure of the resulting powder was characterized by x-ray diffraction which showed the hydrozincite phase as the only phase present. Scanning electron microscope (SEM) examination of the powder showed that it consisted of mesoporous aggregates of primary crystallites. The specific surface area of the powder measured using gas adsorption (BET method, Micromeritics Tristar) was 62.4 $m^2/g$.

The distribution of open pores was measured using gas adsorption techniques (Micromeritics Tristar) according to the Barrett-Joyner-Helenda method (described in Techniques de l'Ingenieur [Techniques of the Engineer] and entitled "Texture des solides poreux ou divises" [Texture of porous or divided solids], p. 3645-1 to 3645-13). The pore size measurements showed a distribution of pore sizes between 2 nm and 100 nm (mesopores) with the average pore size equal to 27.3 nm. The total open mesopore volume was 0.476 $cm^3/g$.

Example 2: Preparation of Mesoporous Zinc Oxide Powder

Zinc oxide powder was prepared from the hydrozincite powder of Example 1 by heat treating at a temperature of 385° C. in an electric kiln. The samples were subject to slow heating with a furnace ramp rate of 100° C./hr and held for 7.5 hours at the set temperature, followed by cooling to room temperature. The resulting powder had an off-white colour. X-ray diffraction showed that ZnO (wurtzite phase) was the only crystalline phase present after calcining.

The heat treated powder was characterized using techniques well known to those skilled in the art and described in greater detail below. A summary of the results are shown in Table 1.

The size distribution of the aggregates was measured using a Malvern Mastersizer 2000 laser scattering instrument. The average aggregate size was 4.1 microns based on volume weighting and 1.1 microns for the number weighted average aggregate size.

The average primary crystallite size measured using x-ray diffraction was 14 nm. The specific surface area was 49.8 $m^2/g$. Porosity measurements showed a mesoporous pore structure. The mesoporosity was of two forms, pores that were closed to the surface (closed porosity) and intercrystalline pores that were open to the surface.

Open pore size measurements using the Barrett-Joyner-Helenda method showed a distribution of sizes between 2 nm and 100 nm with the average open pore size equal to approximately 37 nm. The total open mesopore volume was 0.65 $cm^3/g$.

Values of closed porosity were obtained from measurements of skeletal density using helium gas pycnometry (Micromeritics AccuPyc 1330). The closed porosity was calculated from the skeletal density of the dry zinc oxide aggregates according to the following equation:

Porosity (%)=100×(1−aggregate sample skeletal density/density of ZnO)

wherein, the true density (excluding the volume of open and closed pores) of ZnO=5.606 $g/cm^3$. The pycnometer measurements showed that the closed porosity was 2.6%.

TABLE 1

Summary of ZnO powder characteristics

| Property | Technique | Result |
|---|---|---|
| Average aggregate size (volume average) | Laser Scattering | 4.1 microns (volume distribution) |
| Average aggregate size (number average) | Laser Scattering | 1.1 microns (number distribution) |
| Aggregate Structure | SEM | Aggregates of 15-20 nm primary |
| Primary crystallite size | XRD | 14 nm |
| Specific surface area | BET | 49.8 $m^2$/gram |
| Skeletal density/closed pore volume | Pycnometry | 2.6% (0.0047 $cm^3$/gram) |
| Average open pore size (volume average) | Gas adsorption | 37.3 nm. |
| Open pore volume | Gas adsorption | 0.65 $cm^3$/gram |
| Total Pore Volume | Calculation | 0.655 $cm^3$/gram |

The values of open and closed porosity were used to calculate the total envelope volume and envelope density for the aggregates in air.

In Table 2 values of the total envelope volume, total porosity, and the envelope density for the aggregates in air are compared with the corresponding values for non-porous zinc oxide powder. When both closed and open porosity are included, the total porosity in the aggregates equalled 79% of the total envelope volume and the envelope density of the mesoporous zinc oxide aggregates in air was reduced to 1.19 $g/cm^3$ from the theoretical value for ZnO of 5.606 $g/cm^3$.

TABLE 2

Comparison of volume and density values of aggregates and non-porous ZnO particles

| Property | Non-porous ZnO particles | Aggregates |
|---|---|---|
| Total envelope Volume $cm^3$/g | 0.176 | 0.834 |
| Total porosity | 0 | 79% |
| Envelope density of aggregates in air - $g/cm^3$ | 5.61 | 1.19 |

Example 3: Morphology of Mesoporous Zinc Oxide Powder

Figure 2:
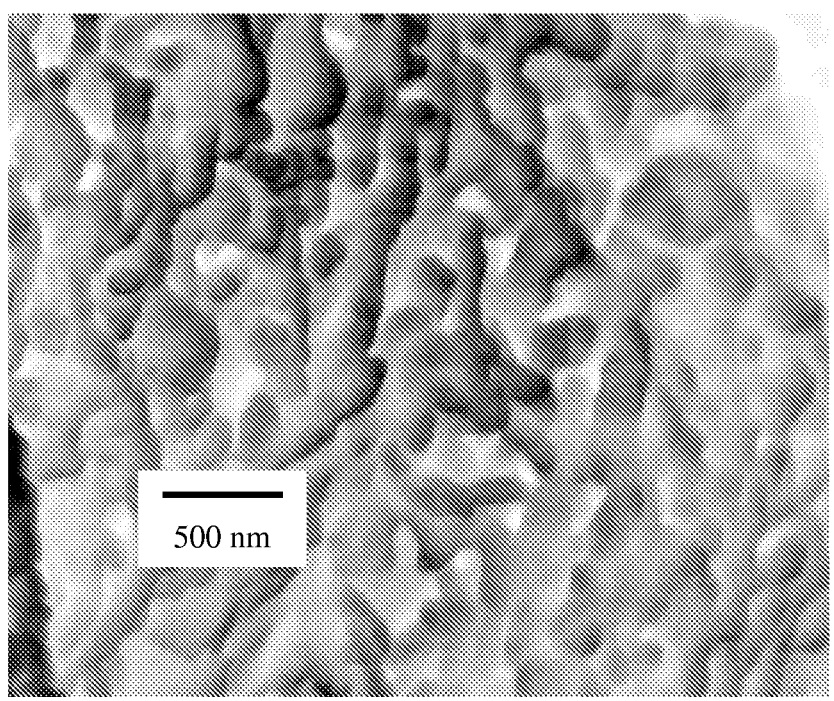
FIG. 2 is a high resolution scanning electron micrograph of the mesoporous zinc oxide powder from Example 1 at a higher magnification showing the open mesopores of the aggregates.

High resolution scanning electron micrographs of mesoporous zinc oxide powder processed from a hydrozincite precursor by heat treating at 425° C. are shown at two different magnifications in FIGS. 1 and 2. The zinc oxide powder consisted of approximately equiaxed aggregates that range in size from about 1 to about 10 microns. As shown in FIG. 2, the aggregates exhibited a mesoporous structure consisting of a plurality of primary crystallites bonded together to form the aggregates, consistent with the results in Example 2.

Example 4: Mesoporous Zinc Oxide Powder Dispersions

The mesoporous zinc oxide powder of Example 3 was dispersed into C12-15 alkyl benzoate using isostearic acid and polyhydroxy stearic acid as dispersants by simple manual mixing.

Figure 3:
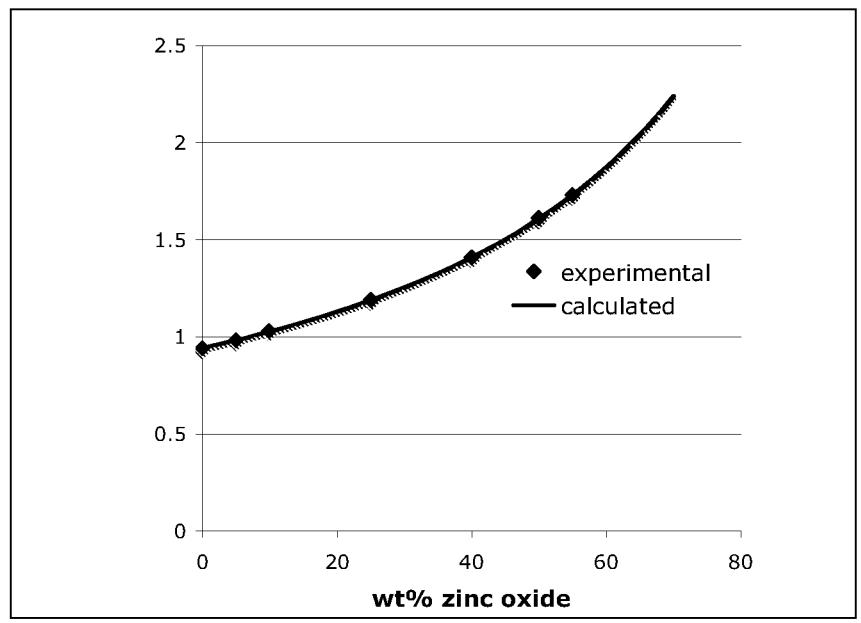
FIG. 3 is a graph showing measurements of the specific gravity of the dispersions of Example 4 plotted as a function of the wt % of zinc oxide as well as a theoretical curve calculated assuming that the open pores are filled with alkyl benzoate.

FIG. 3 shows measurements of the specific gravity of the resulting dispersions plotted as a function of the wt % of ZnO. Also shown is the theoretical curve calculated assuming that the open pores are filled with alkyl benzoate or dispersants (density=0.925 $g/cm^3$) and the closed pores are filled with air (density~0). The excellent agreement between the measured and calculated curves confirmed that the alkyl benzoate filled the open pores in the aggregates.

The values of total porosity were used to calculate envelope density and refractive index of the mesoporous zinc oxide aggregates dispersed in C12-15 alkyl benzoate. The calculation assumes values of refractive index equal to 1.5 and density equal to 0.96 $g/cm^3$ for C12-15 alkyl benzoate. In Table 3 values of the total density and refractive index values for the aggregates are compared with the corresponding values for non-porous zinc oxide particles. The envelope density of the mesoporous zinc oxide powder in C12-15 alkyl benzoate is reduced to 1.92 $g/cm^3$ from its theoretical value of 5.606 $g/cm^3$.

TABLE 3

Comparison of volume and density values of aggregates and non-porous ZnO particles

| Property | Non-porous ZnO particles | Aggregates |
|---|---|---|
| Envelope Density - oil ($g/cm^3$) | 5.606 | 1.92 |
| Refractive Index | 2.01 | 1.59 |

Example 5: Effect of Milling on Aggregate Size

Dispersions formed according to Example 4 were milled in a laboratory bead mill. The average aggregate size before and after the bead milling was measured using Laser Scattering (Malvern Mastersizer 2000). Table 4 shows the effect of bead milling time on the average aggregate size of a 50 wt % of the mesoporous zinc oxide powder dispersed in alkyl benzoate. The milling caused a reduction in aggregate size as would be understood by one versed in the art.

TABLE 4

Effect of bead milling on aggregate size

| Milling Time (hrs) | Volume average aggregate size (μm) | Number average aggregate size (μm) |
|---|---|---|
| 0 | 9.3 | 1.19 |
| 4 | 5.1 | 1.00 |

Figure 4:
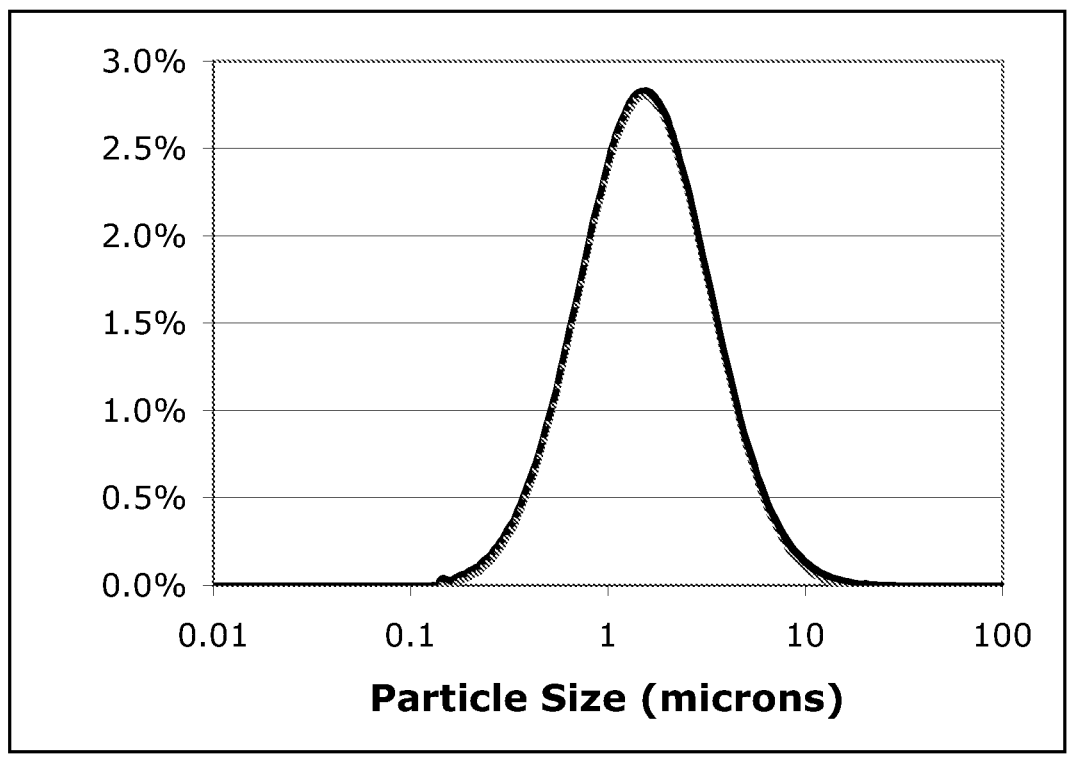
FIG. 4 shows the number weighted distribution of particle sizes for a dispersion of milled mesoporous zinc oxide in Caprylic Capric Triglyceride measured using acoustic attenuation (Dispersion Technology DT1200).

A second dispersion was formed according to Example 4 with the exception that Caprylic Capric Triglyceride (CCT) was used as the carrier. The dispersion was milled in a bead mill. Particle size measurements were carried out using Laser Scattering and Acoustic Attenuation (Dispersion Technology DT-1200). FIG. 4 shows the number weighed particle size distribution curve obtained using Acoustic Attenuation. The number weighted average size distribution obtained using Acoustic Attenuation was 1.55 microns as compared to the value of 1.17 microns measured using Laser Scattering. No aggregates having sizes less than 0.100 microns were detected using either technique for this second dispersion either prior to or after bead milling.

To confirm that the plurality of zinc oxide crystallites are bonded together to form aggregates rather than a loose agglomeration, a pre-mixed dispersion of 50 wt % of the zinc oxide aggregates in alkyl benzoate was subjected to high shear mixing under the following conditions:

Mixer: Silverson L4RT
Mixing speed: 7000 rpm
Mixing time: 20 minutes
Sample volume: 60 ml The average aggregate size before and after the high mixing was measured using a Malvern Mastersizer 2000. No significant change in the average aggregate size was observed after the high shear mixing. A difference between agglomerates and aggregates is that high shear mixing is sufficient to break apart an agglomerate, whilst the average size of an aggregate will show little difference. The results shown in Table 4 above demonstrate that the zinc oxide powder of the present invention is in aggregate form.

Example 6: Optical Properties

The optical properties of the dispersions of Example 5 were evaluated using UV/visible spectral measurements. The optical properties of the dispersions, specifically, total transparency, total absorptance and CIE whiteness index are listed below in Table 5.

The term "total absorptance" as used throughout this specification is defined mathematically using the following equation:

$$A = -\ln(T(\%)/100)$$

Where
 A is the total absorptance
 T is the total transmittance at 550 nm wavelength measured as a percentage Each of the dispersions was placed in a quartz cell of 20 microns in optical path length. Optical transmittance and reflectance measurements were carried out using a Carey 300 bio UV-Vis spectrophotometer equipped with an integrating sphere. The total extinction coefficient was calculated from the total transmittance values using the above equations. The CIE whiteness index values of the formulations were calculated from reflectance values according to the Australian standard ASTM-E313.

For comparison purposes, Table 5 also includes data for prior art formulations comprising 40-60 wt % of the following types of zinc oxide single crystallite particles:
 a) silicone-coated ZnO nanoparticles having an average particle diameter of ~30 nm prepared using the method described in U.S. Pat. No. 6,503,475;
 b) stearic-acid coated ZnO nanoparticles having an average particle size of ~30 nm prepared using the method described in U.S. Pat. No. 6,503,475;
 c) silica-coated ZnO nanoparticles having an average particle size of 82 nm prepared using the method described in U.S. Pat. No. 5,587,148.

Formulations of the present invention comprising mesoporous aggregates have significantly higher transparencies and lower whiteness values than the comparative prior art formulations in spite of the significantly larger size of the aggregates. This results in lower extinction coefficients (less than 0.05) and lower whiteness (less than 25) values. Whilst bead milling resulted in an improvement of transparency and whiteness, milling was not required to achieve values of transparency and whiteness that exceed the prior art formulations.

TABLE 5

Optical Properties

| | As Mixed | After Bead milling | Silicone-coated ZnO nanoparticles | Stearic acid coated ZnO nanoparticles | Silica coated ZnO nanoparticles |
|---|---|---|---|---|---|
| Zinc oxide concentration (wt %) | 50 | 50 | 60 | 40 | 50 |
| Aggregate/particle Size (microns) Number average | 1.081 | 0.942 | 0.035 | 0.035 | .080 |
| Total Transmittance at 550 nm (%) | 84.8 | 87.3 | 82.0 | 70.5 | 50.8 |
| Total absorptance at 550 nm | 0.165 | 0.136 | 0.198 | 0.350 | 0.677 |
| CIE Whiteness index | 28 | 26 | 34 | 53 | 60 |

Example 7: Effect of Reaction Chemistry (Counter Example to Example 1)

Zinc carbonate precursor powders were synthesized by reacting aqueous solutions of zinc chloride and sodium carbonate following the procedure of Example 1 with the exception that molar ratios of $ZnCl_2:Na_2CO_3$ of 1:2 and 1:1 were employed.

The resulting powders were characterized by x-ray diffraction which showed that hydrozincite was the only phase present in both the 1:2 and 1:1 molar ratio samples.

The powders were then heat treated at 380° C. for 7 hours, resulting in a white powder. Using x-ray diffraction, ZnO (wurtzite) was identified as the only crystallite phase.

The properties of the powders and dispersions prepared from the powders are summarised in Table 6. The values of pore volume decreased with decreasing $ZnCl_2:Na_2CO_3$ molar ratio. The smaller pore volumes for the 1:1 and 1:2 molar ratios are reflected in larger values of envelope density and refractive index.

Samples synthesized with 1:1 molar ratio of $ZnCl_2:Na_2CO_3$ also showed a significantly decreased average aggregate size of 0.204 microns in comparison to the average aggregate sizes of the samples with 1:3 and 1:2 molar ratios.

The whiteness index and extinction coefficient of the sample prepared with the 1:1 ratio of $ZnCl_2:Na_2CO_3$ were significantly reduced due to the reduction in total pore volume and refractive index. In spite of the reduced scattering associated with the small particle size, the whiteness index of the 1:1 ratio sample was 37.0 as compared with 20.1 for the 1:3 ratio and 17.1 for the 1:2 ratio. Similarly, the 1:1 ratio sample exhibited a ~50% increase in the extinction coefficient as compared to the 1:3 molar ratio.

The results demonstrate that a reaction stoichiometry of $ZnCl_2:Na_2CO_3$ molar ratio of 1:2 or higher) is required when synthesizing mesoporous zinc oxide aggregates to achieve the combination of large aggregate size, large total mesoporous pore volume, low whiteness and high transparency of the present invention.

TABLE 6

Summary of effect of molar ratio on aggregate properties

| Property | $ZnCl_2$ and $Na_2CO_3$ Molar ratio | | |
| --- | --- | --- | --- |
| | 1:3 | 1:2 | 1:1 |
| Average particle size (microns) number weighted | 1.09 | 1.02 | 0.20 |
| Average open mesopore size (nm) | 37.3 | 33.2 | 40.7 |
| Open mesopore volume (m³/g) | 0.65 | 0.45 | 0.28 |
| Total pore volume (cm³/g) | 0.655 | 0.455 | 0.295 |
| Envelope Density (g/cm³) (in C12-15 alkyl benzoate) | 1.92 | 2.22 | 2.68 |
| Whiteness index | 20.1 | 17.1 | 37.0 |

Example 8: Effect of Pore Volume on Transparency and Whiteness

Samples of zinc oxide aggregates containing different pore volumes were prepared according to Example 2, except that heat treatment temperature was varied between 385° C. and 625° C.

Figure 5:
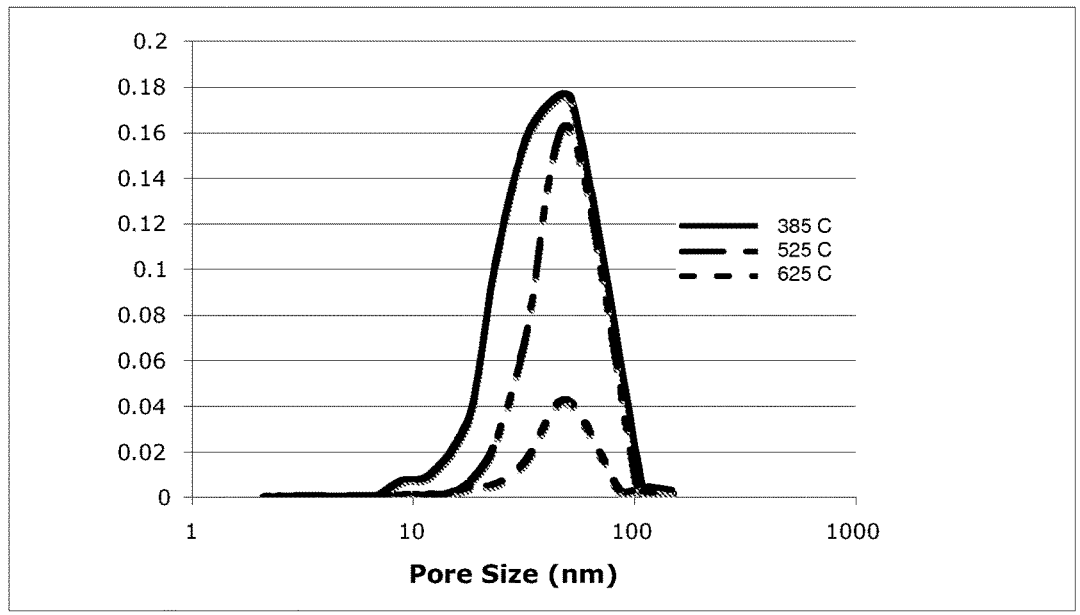
FIG. 5 shows the effect of heat treatment temperature on the distribution of open pores.
Figure 6:
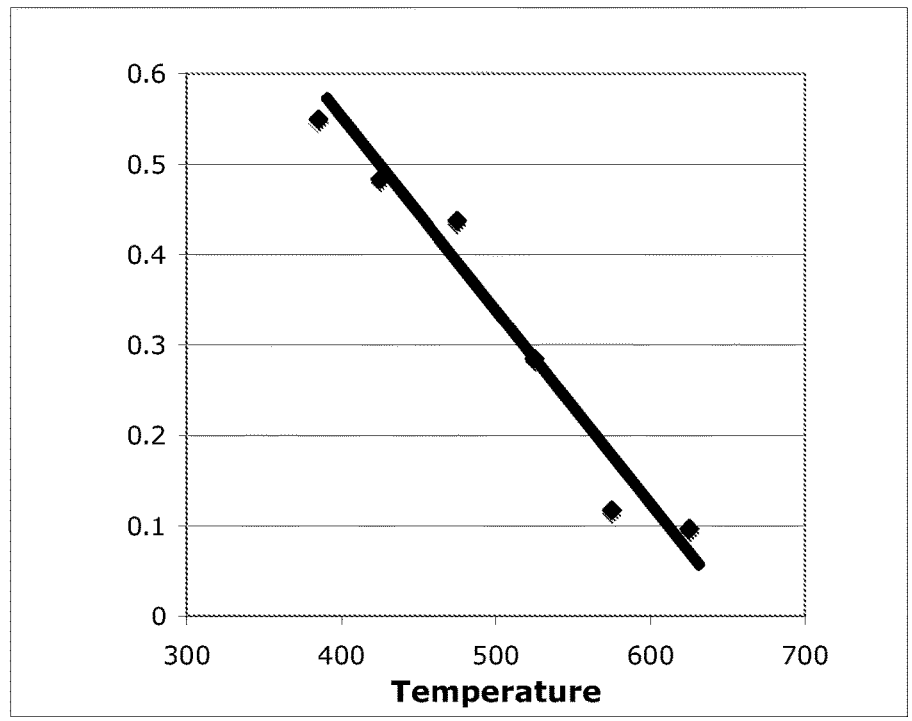
FIG. 6 illustrates graphically the relationship between the pore volume and heat treatment temperature.

FIG. 5 shows the effect of heat treatment temperature on the distribution of open pores. The pore size distributions are unimodal. The average pore size did not change significantly with temperature. However, as shown in FIG. 6, the volume of the mesopores pores decreased significantly with increasing temperature due to sintering of the crystallites. The effect of heat treatment temperature on pore volume is shown in FIG. 5.

Figure 7:
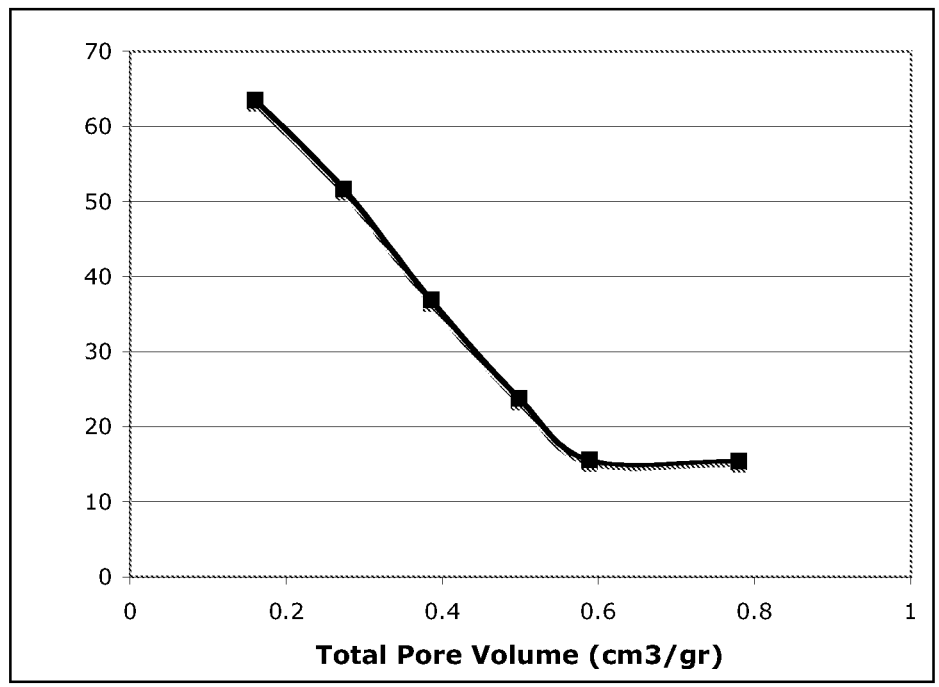
FIG. 7 illustrates graphically the effect of total pore volume on the whiteness index of dispersions formed according to Example 4.
Figure 8:
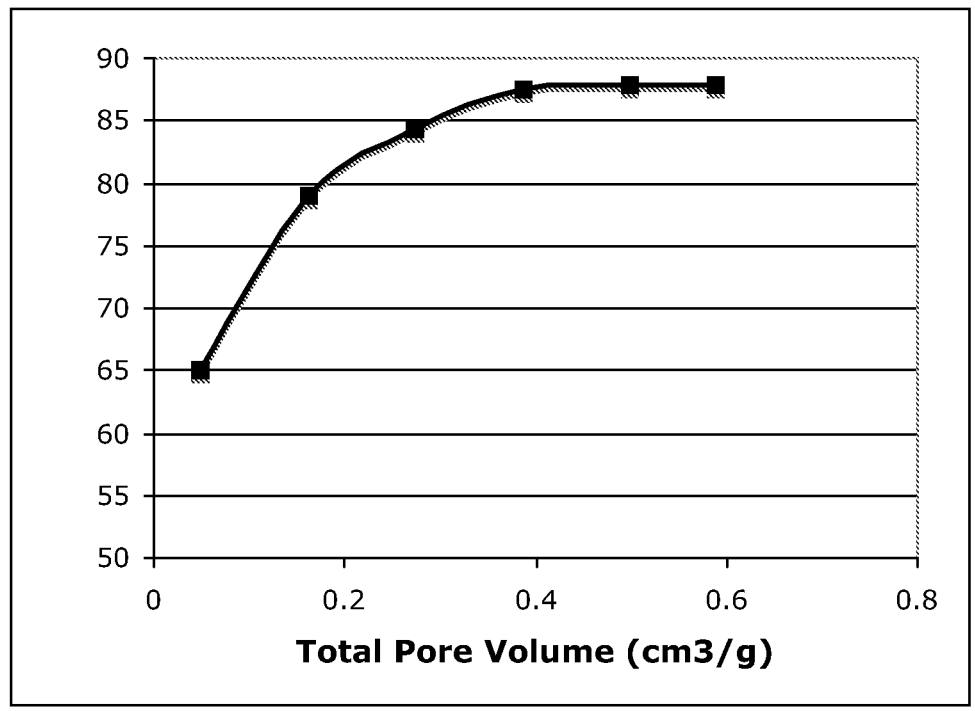
FIG. 8 illustrates graphically the effect of total pore volume on the total visible transmittance of dispersions formed according to Example 4.

FIGS. 7 and 8 show the effect of total pore volume on the whiteness index and total visible transmittance, respectively of dispersions formed according to Example 4. It is seen that low whiteness and high transmittance values require a sufficiently large total pore volume. The results of Examples 7 and 8 demonstrate the critical importance of pore volume to achieving low whiteness and high transparency in micron size mesoporous aggregates.

It is expected that other methods of achieving large mesopore volume, in addition to reaction stoichiometry and heat treatment conditions, will also provide powders for low whiteness and high transparency formulations Example 9: Effect of Zinc Oxide Concentration on Optical Properties Dispersions containing 2.5% to 50 wt % mesoporous ZnO in Caprylic Capric Triglyceride were prepared using a laboratory bead mill. Optical transmittance measurements were carried out using a Carey 300 bio UV-Vis spectrophotometer equipped with an integrating sphere. The samples were placed in a quartz cell having optical path length of 0.02 mm.

Figure 9:
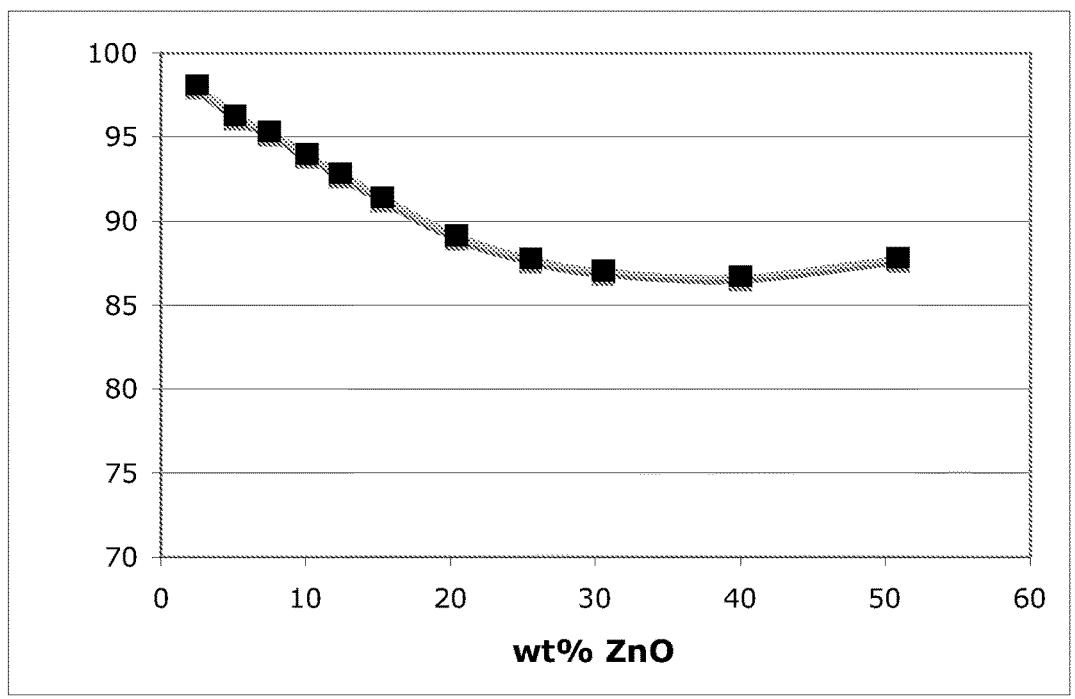
FIG. 9 illustrates graphically the effect of ZnO concentration on total visible transmittance; and, FIG. 10 illustrates graphically the effect of ZnO concentration on the CIE whiteness index.
Figure 10:
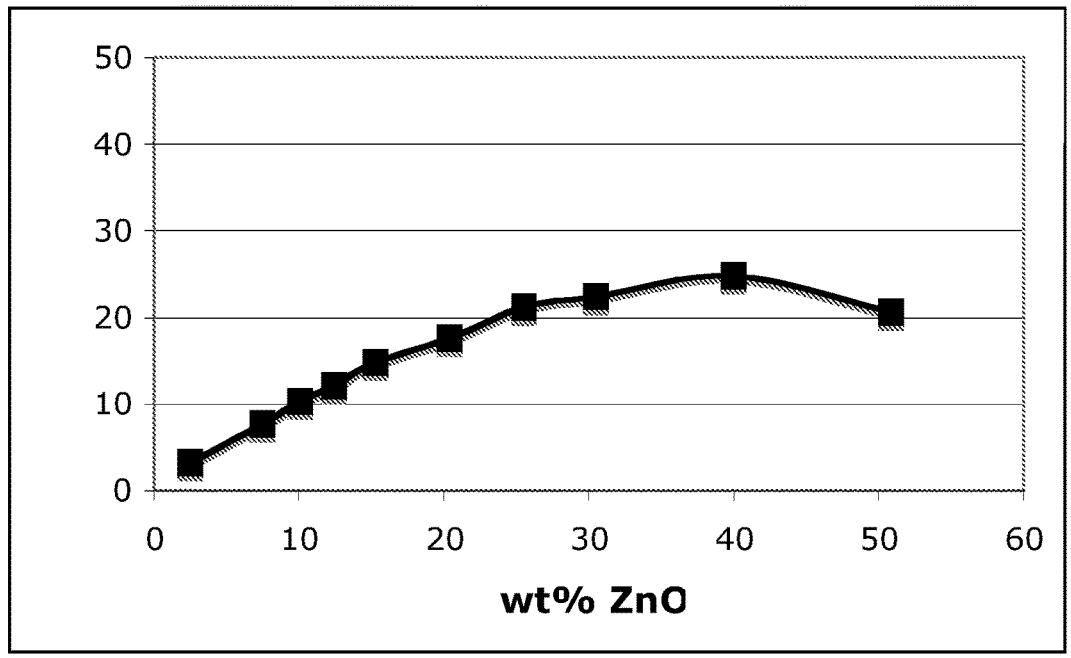

FIG. 9 shows the effect of zinc oxide concentration on the total visible light transmittance. The transmittance measurements were taken at a wavelength of 550 nm (middle of visible spectrum) and the path length (cell thickness) is 20 microns. The results show that the transmittance initially decreased and then leveled out for zinc oxide concentrations greater than 25 wt %. A similar levelling out was also observed in measurements of the CIE whiteness index as shown in FIG. 10.

It will be apparent to persons skilled in the relevant art that numerous variations and modifications can be made without departing from the basic inventive concepts. For example, the open pores of the aggregates can be filled with a medicament in fluid form followed by coating of the aggregate with an enteric coating to encase the medicament within the mesoporous zinc oxide powder for delayed release in use. All such modifications and variations are considered to be within the scope of the present invention, the nature of which is to be determined from the foregoing description and the appended claims.

What is claimed:

1. A method of manufacturing a mesoporous zinc oxide powder comprising:
 synthesizing a mesoporous zinc oxide precursor powder by a step consisting essentially of adding an aqueous solution of zinc chloride to an aqueous solution of sodium carbonate while agitating to cause precipitation of a mesoporous zinc carbonate powder, wherein the molar ratio of zinc chloride to sodium carbonate present when the aqueous solution of zinc chloride and the aqueous solution of sodium carbonate are reacted is such that at least 2 moles of sodium carbonate are present for each 1 mole of zinc chloride; and
 heat treating the mesoporous zinc oxide precursor powder to form the mesoporous zinc oxide powder at a heat treatment temperature in the range of 250-575° C.;
 wherein the mesoporous zinc oxide powder comprises mesoporous zinc oxide aggregates comprising a plurality of primary zinc oxide crystallites bonded together at shared interfaces, the aggregates having a number average aggregate size of at least 0.8 micron, wherein the aggregates have a total mesopore volume of at least 0.5 cm$^3$/g, a pore size in the range of 2 nm to 100 nm, and, a surface area in the range of 20 to 70 m$^2$/g.

2. The method of manufacturing the zinc oxide powder of claim 1, wherein the molar ratio of zinc chloride to sodium carbonate present when the aqueous solution of zinc chloride and the aqueous solution of sodium carbonate are reacted is such that at least 3 moles of sodium carbonate are present for each 1 mole of zinc chloride.

3. The method of manufacturing the zinc oxide powder of claim 1, wherein the heat treatment temperature is in the range of 300-525° C. or in the range of 350-475° C. or in the range of 400-450° C.

4. The method of claim 1, wherein the aggregates have a number average aggregate size of at least 1 micron.

5. The method of claim 1, wherein the zinc oxide powder produces a transparent composition having a total visible transmittance through a path length of 20 microns at 550 nm of at least one of at least 70%, at least 75%, at least 80%, at least 85%, and at least 93% in a dispersion at a concentration of at least 10 wt % of zinc oxide.

6. The method of claim 1, wherein the zinc oxide powder produces a transparent composition having a total visible transmittance through a path length of 20 microns at 550 nm of at least one of at least 70%, at least 75%, at least 80% and at least 88% in a dispersion at a concentration of at least 20 wt % of zinc oxide.

7. The method of claim 1, wherein the zinc oxide powder produces a transparent composition having a total visible transmittance through a path length of 20 microns at 550 nm of at least one of at least 70%, at least 75%, at least 80% and at least 85% in a dispersion at a concentration of at least 30 wt % of zinc oxide.

8. The method of claim 1, wherein the zinc oxide powder produces a transparent composition having a total visible transmittance through a path length of 20 microns at 550 nm of at least one of at least 70%, at least 75%, at least 80% and at least 85% in a dispersion at a concentration of at least 40 wt % of zinc oxide.

9. The method of claim 1, wherein the zinc oxide powder produces a transparent composition having a total visible transmittance through a path length of 20 microns at 550 nm of at least one of at least 75%, at least 80%, and at least 85% in a dispersion at a concentration of at least 50 wt % of zinc oxide.

10. The method of claim 1, wherein the zinc oxide powder produces a CIE whiteness index less than 30, or less than 40, or less than 50 in a dispersion at a concentration of at least 50 wt % of zinc oxide.

11. The method of claim 1, wherein the zinc oxide powder produces a CIE whiteness index less than 25, or less than 35, or less than 45 in a dispersion at a concentration of at least 20 wt % of zinc oxide.

12. The method of claim 1, wherein the zinc oxide powder produces a CIE whiteness index less than 25, or less than 35, or less than 45 in a dispersion at a concentration of at least 30 wt % of zinc oxide.

13. The method of claim 1, wherein the aggregates have sizes in the range of 0.1 micron to 100 microns.

14. The method of claim 1, wherein the number average zinc oxide aggregate size is compared with a target aggregate size and reduced using milling if the number average zinc oxide aggregate size is larger than the target aggregate size.

15. The method of claim 1, further comprising the step of adjusting the refractive index of the zinc oxide powder by filling the open mesopores of the aggregates with a substance other than air.

* * * * *